United States Patent [19]

Erilli

[11] Patent Number: 5,780,411
[45] Date of Patent: Jul. 14, 1998

[54] HIGH FOAMING NONIONIC SURFACTANT BASED LIQUID DETERGENT

[75] Inventor: Rita Erilli, Liege, Belgium

[73] Assignee: Colgate-Palmolive Company, Piscataway, N.J.

[21] Appl. No.: 871,484

[22] Filed: Jun. 9, 1997

Related U.S. Application Data

[63] Continuation-in-part of Ser. No. 412,322, Apr. 3, 1995, abandoned.

[51] Int. Cl.$^6$ .................. C11D 1/02; C11D 1/29; C11D 1/72; C11D 1/90
[52] U.S. Cl. .......... 510/237; 510/235; 510/423; 510/424; 510/427; 510/428; 510/433; 510/502
[58] Field of Search .................. 510/235, 423, 510/424, 427, 428, 433, 237, 502

[56] References Cited

U.S. PATENT DOCUMENTS

| 4,595,526 | 6/1986 | Lai | 252/545 |
| 4,728,457 | 3/1988 | Fieler et al. | 252/174.15 |
| 4,854,333 | 8/1989 | Inman et al. | 132/209 |
| 4,867,971 | 9/1989 | Ryan et al. | 424/81 |
| 5,385,696 | 1/1995 | Repinec, Jr. et al. | 252/546 |
| 5,387,375 | 2/1995 | Erilli et al. | 252/546 |
| 5,389,304 | 2/1995 | Repinec, Jr. et al. | 252/546 |
| 5,389,305 | 2/1995 | Repinec et al. | 252/546 |
| 5,610,127 | 3/1997 | Erilli et al. | 510/235 |

*Primary Examiner*—Paul Lieberman
*Assistant Examiner*—Gregory R. Delcotto
*Attorney, Agent, or Firm*—Richard E. Nanfeldt; James M. Serafino

[57] ABSTRACT

A high foaming, nonionic surfactant based, light duty, liquid detergent with desirable cleansing properties and mildness to the human skin comprising: a water soluble nonionic surfactant as the major active ingredient, in an amount in excess of 40% by weight of the total surfactant content; a water soluble, foaming, anionic sulfate, a water soluble, foaming zwitterionic betaine surfactant, a pearlescing agent and the balance being water.

9 Claims, No Drawings

HIGH FOAMING NONIONIC SURFACTANT BASED LIQUID DETERGENT

RELATED APPLICATION

This application is a continuation in part application of U.S. Ser. No. 8/412,322 filed Apr. 3, 1995 now abandoned.

BACKGROUND OF THE INVENTION

The present invention relates to novel light duty liquid detergent compositions with high foaming properties and having a pearlescence appearance. These compositions contain a nonionic surfactant as the major active ingredient supplemented with lesser amounts of an anionic sulfate surfactant, an ethoxylated alkyl ether sulfate surfactant, a zwitterionic betaine surfactant, an ethylene glycol distearate, and a mixture of fatty acid monoalkanol amide and a $C_{12}EO_{10}$ surfactant in an aqueous medium.

Nonionic surfactants are in general chemically inert and stable toward pH change and are therefore well suited for mixing and formulation with other materials. The superior performance of nonionic surfactants on the removal of oily soil is well recognized. Nonionic surfactants are also known to be mild to human skin. However, as a class, nonionic surfactants are known to be low or moderate foamers. Consequently, for detergents which require copious and stable foam, the application of nonionic surfactants is limited. There have been substantial interest and efforts to develop a high foaming detergent with nonionic surfactants as the major ingredient. Yet, little has been achieved.

The prior art is replete with light duty liquid detergent compositions containing nonionic surfactants in combination with anionic and/or betaine surfactants wherein the nonionic detergent is not the major active surfactant. In U.S. Pat. No. 3,658,985 an anionic based shampoo contains a minor amount of a fatty acid alkanolamide. U.S. Pat. No. 3,769,398 discloses a betaine-based shampoo containing minor amounts of nonionic surfactants. This patent states that the low foaming properties of nonionic detergents renders its use in shampoo compositions non-preferred. U.S. Pat. No. 4,329,335 also discloses a shampoo containing a betaine surfactant as the major ingredient and minor amounts of a nonionic surfactant and of a fatty acid mono- or diethanolamide. U.S. Pat. No. 4,259,204 discloses a shampoo comprising 0.8 to 20% by weight of an anionic phosphoric acid ester and one additional surfactant which may be either anionic, amphoteric, or nonionic. U.S. Pat. No. 4,329,334 discloses an anionic-amphoteric based shampoo containing a major amount of anionic surfactant and lesser amounts of a betaine and nonionic surfactants.

U.S. Pat. No. 3,935,129 discloses a liquid cleaning composition containing an alkali metal silicate, urea, glycerin, triethanolamine, an anionic detergent and a nonionic detergent. The silicate content determines the amount of anionic and/or nonionic detergent in the liquid cleaning composition. However, the foaming properties of these detergent compositions are not discussed therein.

U.S. Pat. No. 4,129,515 discloses a heavy duty liquid detergent for laundering fabrics comprising a mixture of substantially equal amounts of anionic and nonionic surfactants, alkanolamines and magnesium salts, and, optionally, zwitterionic surfactants as suds modifiers.

U.S. Pat. No. 4,224,195 discloses an aqueous detergent composition for laundering socks or stockings comprising a specific group of nonionic detergents, namely, an ethylene oxide of a secondary alcohol, a specific group of anionic detergents, namely, a sulfuric ester salt of an ethylene oxide adduct of a secondary alcohol, and an amphoteric surfactant which may be a betaine, wherein either the anionic or nonionic surfactant may be the major ingredient.

The prior art also discloses detergent compositions containing all nonionic surfactants as shown in U.S. Pat. Nos. 4,154,706 and 4,329,336 wherein the shampoo compositions contain a plurality of particular nonionic surfactants in order to affect desirable foaming and detersive properties despite the fact that nonionic surfactants are usually deficient in such properties.

U.S. Pat. No. 4,013,787 discloses a piperazine based polymer in conditioning and shampoo compositions which may contain all nonionic surfactant or all anionic surfactant.

U.S. Pat. No. 4,450,091 discloses high viscosity shampoo compositions containing a blend of an amphoteric betaine surfactant, a polyoxybutylenepolyoxyethylene nonionic detergent, an anionic surfactant, a fatty acid alkanolamide and a polyoxyalkylene glycol fatty ester. But, none of the exemplified compositions contain an active ingredient mixture wherein the nonionic detergent is present in major proportion which is probably due to the low foaming properties of the polyoxybutylene polyoxyethylene nonionic detergent.

U.S. Pat. No. 4,595,526 describes a composition comprising a nonionic surfactant, a betaine surfactant, an anionic surfactant and a $C_{12}$–$C_{14}$ fatty acid monoethanolamide foam stabilizer.

U.S. Pat. No. 4,867,971 relates to an antidandruff shampoo contains a sodium ethoxylated alkyl ether sulfate at a concentration of 6 to 25% and EUPERLAN PK771™. U.S. Pat. No. 5,348,736 also teaches hair treating composition containing EUPERLAN PK771™.

However, none of the above-cited patents discloses a high foaming, nonionic based, liquid detergent composition having a pearlescence appearance and containing a nonionic surfactant as a major active ingredient and minor amounts of an anionic sulfate surfactant, an ethoxylated alkyl ether sulfate surfactant, an ethylene glycol distearate, a mixture of an alkyl monoalkanol amide and a $C_{12}EO_{10}$ surfactant which is different from the nonionic surfactant and a zwitterionic surfactant selected from betaine type surfactants, wherein the nonionic ingredient constitutes more than 50 wt. % of the total surfactant content.

SUMMARY OF THE INVENTION

It has now been found that a high foaming liquid detergent having a pearlescence appearance can be formulated with a nonionic surfactant as the major active ingredient which has desirable cleaning properties and mildness to the human skin.

Accordingly, one object of this invention is to provide novel, high foaming, nonionic based, light duty liquid detergent compositions containing a nonionic surfactant at a concentration of at least 40 wt. % of the total surfactant content.

Another object of this invention is to provide novel, nonionic based, liquid detergent compositions containing a major amount of nonionic surfactant supplemented with lesser amounts of an anionic sulfate surfactant, an ethoxylated alkyl ether sulfate surfactant, a zwitterionic betaine surfactant, a mixture of a $C_{12}EO_{10}$ surfactant and a fatty acid monoalkanol amide and an ethylene glycol distearate, wherein the $C_{12}E_{10}$ surfactant is different from the nonionic surfactant.

Still Another object of this invention is to provide a novel, nonionic based, liquid detergent with desirable high foaming and cleaning properties which is mild to the human skin.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects and in accordance with the purpose of the present invention, as embodied and broadly described herein the novel, high foaming, nonionic based, light duty liquid detergent of this invention comprises a mixture of a fatty acid monoalkanol amide and a $C_{12}EO_{10}$ surfactant and an ethylene glycerol distearate in combination with four essential surfactants which are a water soluble, ethoxylated, nonionic surfactant as the major active ingredient in an amount exceeding 40% by weight of the total surfactant content; a supplemental amount of a foaming anionic sulfate surfactant, an ethoxylated alkyl ether sulfate surfactant, and a foaming water soluble, zwitterionic surfactant selected from the class of betaines dissolved in an aqueous vehicle wherein the composition does not contain any polyoxyalkylene glycol fatty ester.

More specifically, the present invention relates to a high foaming, nonionic based, liquid detergent containing more than 50% by weight of the total surfactant content of a nonionic surfactant selected from the group consisting of water soluble primary aliphatic alcohol ethoxylates, secondary aliphatic alcohol ethoxylates, alkyl phenol ethoxylates and alcohol ethylene oxide propylene oxide condensates; and supplementary amounts of an anionic surfactant which is a water soluble salt of a $C_8$–$C_{18}$ alkyl sulfate surfactant, an ethoxylated alkyl ether sulfate surfactant, a mixture of a $C_{12}EO_{10}$ surfactant and a $C_{12}$–$C_{14}$ fatty acid monoethanol amide, an ethylene glycol distearate; and a water soluble zwitterionic betaine surfactant, the total content of said ethylene glycol distearate, said anionic sulfate surfactant, said ethoxylated alkyl ether sulfate surfactant, said $C_{12}EO_{10}$ said fatty acid monoethanol amide, and said betaine surfactant, constituting less that 50% by weight of the total surfactant content, dissolved in an aqueous vehicle.

This particular combination of ingredients in the proportions, by weight, of: 10 to 30% of a nonionic surfactant wherein said nonionic surfactant is in excess of 50% by weight of the total surfactant content, 1 to 10% by weight of an anionic sulfate surfactant, 0.5 to 10% by weight of a betaine surfactant, 0.5 to 3% of an ethoxylated ether sulfate surfactant, 0.2 to 3 wt. % of a mixture of a $C_{12}EO_{10}$ surfactant and a $C_{12}$–$C_{14}$ fatty acid monoalkanol amide such as a $C_{12}$–$C_{14}$ fatty acid monoethanolamide; 0.5 to 3 wt. % of an ethylene glycol distearate and the balance being water, wherein the nonionic constitutes at least 40 wt. percent of the total surfactant content is critical to the high foaming and desirable cleansing properties of present liquid detergent and the retention of the mildness to the skin property. The total amount of surfactants may constitute 17.5% to 51%, preferably 20% to 40%, most preferably 25% to 35%, by weight of the liquid composition. Excluded from the instant compounds are polyoxyalkylene glycol fatty esters, abrasives, polymeric thickeners, clay thickeners, silica, abrasive, clays, alkali metal carbonates or more than 3 wt. % of a fatty acid or its salt thereof.

DETAILED DESCRIPTION OF THE INVENTION

The present invention relates to a light duty liquid detergent having a pearlescence appearance which comprises approximately by weight:

(a) 10% to 30% of a nonionic surfactant;

(b) 1% to 10% of an alkyl sulfate surfactant;

(c) 0.5% to 10% of an alkyl betaine surfactant;

(d) 0.5% to 3% of ethylene glycol distearate;

(e) 0.2% to 3% of a mixture of a $(CH_2)_xEO_y$ surfactant and a $C_{12\text{-}14}$ fatty acid monoalkanol amide, wherein the $(CH_2)_xEO_y$ surfactant is different from the water soluble nonionic surfactant and the weight ratio of $(CH_2)_xEO_y$ surfactant to said $C_{12\text{-}14}$ fatty acid monoalkanol amide is about 3:1 to about 1:3 and x is 10 to 14 and y is 8 to 12;

(f) 0.5% to 3.0% of an ethoxylated alkyl ether sulfate surfactant; and (g) the balance being water, wherein the combination of the $(CH_2)_xEO_y$ nonionic surfactant; the $C_{12\text{-}14}$ fatty acid monoalkanol amide, the ethoxylated alkyl ether sulfate surfactant and the ethylene glycol distearate is commercially available from Henkel as EUPERLAN PK771™ as a pearlescing agent and this combination imparts a pearlescence appearance to the composition. Excluded from the instant compositions are cetearyl alcohol, tricetyl methyl ammonium chloride, a silicone conditioning agent such as polydimethyl siloxane, polyalkyl siloxane, polyaryl siloxane, polyalkylaryl siloxane, polyether siloxane copolymer, peroxy oxidizing agents such as hydrogen peroxide and sodium percarbonate, sodium perborate and perbenzoic acid, and selenium sulfide.

Other pearlescing agents which are based upon ethylene glycol distearate, PEG-3 distearate, glyceryl stearate or ethylene glycol monostearate are: EUPERLAN PK3000™ told by Henkel which is a mixture of ethylene glycol distearate, cocoamidopropyl betaine and an ethoxylated fatty alcohol; EUPERLAN PK900™ sold by Henkel which is a mixture of an ethoxylated alkyl ether sulfate and PEG-3-distearate; Lamesoft 156 sold by Henkel which is a mixture of glyceryl stearate and potassium cocoylhydrolyzed collagen; EMPICOL 0627/F™ sold by Albright and Wilson which is a mixture of ethylene glycol monostearate, ethoxylated alkyl ether sulfate and cocodiethanol amide; and TEGO PEARL B48™ sold by Goldschmidt which is a mixture of ethylene glycol distearate; cocoamidopropyl betaine, cocomonoethanol amide and cocodiethanolamide.

The nonionic surfactant which constitutes the major ingredient in present liquid composition is present in amounts of 10% to 30%, preferably 13% to 25%, most preferably 16% to 22%, by weight of the composition and provides superior performance in the removal of oily soil and mildness to human skin.

The water soluble nonionic surfactants utilized in this invention are commercially well known and include the primary aliphatic alcohol ethoxylates, secondary aliphatic alcohol ethoxylates, alkylphenol ethoxylates and ethyleneoxide-propylene oxide condensates of primary alkanols, such a Plurafacs (BASF) and condensates of ethylene oxide with sorbitan fatty acid esters such as the Tweens (ICI). The nonionic synthetic organic surfactants generally are the condensation products of an organic aliphatic or alkyl aromatic hydrophobic compound and hydrophilic ethylene oxide groups. Practically any hydrophobic compound having a carboxy, hydroxy, amido, or amino group with a free hydrogen attached to the nitrogen can be condensed with ethylene oxide or with the polyhydration product thereof, polyethylene glycol, to form a water-soluble nonionic detergent. Further, the length of the polyethenoxy chain can be adjusted to achieve the desired balance between the hydrophobic and hydrophilic elements.

The nonionic detergent class includes the condensation products of a higher alcohol (e.g., an alkanol containing 8 to 18 carbon atoms in a straight or branched chain configuration) condensed with 5 to 30 moles of ethylene oxide, for example, lauryl or myristyl alcohol condensed with 16 moles of ethylene oxide (EO), tridecanol condensed with 6 to 12 moles of EO, myristyl alcohol condensed with about 10 moles of EO per mole of myristyl alcohol, the condensation product of EO with a cut of coconut fatty alcohol containing a mixture of fatty alcohols with alkyl chains varying from 10 to 14 carbon atoms in length and wherein the condensate contains either 6 moles of EO per mole of total alcohol or 9 moles of EO per mole of alcohol and tallow alcohol ethoxylates containing 6 EO to 11 EO per mole of alcohol.

A preferred group of the foregoing nonionic surfactants are the Neodol ethoxylates (Shell Co.), which are higher aliphatic, primary alcohols containing about 9 to 15 carbon atoms, such as $C_9$–$C_{11}$ alkanol condensed with 8 moles of ethylene oxide (Neodol 91-8), $C_{12-13}$ alkanol condensed with 6.5 moles ethylene oxide (Neodol 23-6.5), $C_{12-15}$ alkanol condensed with 12 moles ethylene oxide (Neodol 25-12), $C_{14-15}$ alkanol condensed with 13 moles ethylene oxide (Neodol 45-13), and the like. Such ethoxamers have an HLB (hydrophobic lipophilic balance) value of 8 to 15 and give good emulsification, whereas ethoxamers with HLB values below 8 contain less than 5 ethyleneoxy groups and tend to be poor emulsifiers and poor surfactants. Other preferred nonionic surfactants are Dobanol 1-9 and Dobanol 91-8.

Additional satisfactory water soluble alcohol ethylene oxide condensates are the condensation products of a secondary aliphatic alcohol containing 8 to 18 carbon atoms in a straight or branched chain configuration condensed with 5 to 30 moles of ethylene oxide. Examples of commercially available nonionic surfactants of the foregoing type are $C_{11}$–$C_{15}$ secondary alkanol condensed with either 9 EO (Tergitol 15-S-9) or 12 EO (Tergitol 15-S-12) marketed by Union Carbide.

Other suitable nonionic surfactants include the polyethylene oxide condensates of one mole of alkyl phenol containing from 8 to 18 carbon atoms in a straight- or branched chain alkyl group with 5 to 30 moles of ethylene oxide. Specific examples of alkyl phenol ethoxylates include nonyl condensed with 9.5 moles of EO per mole of nonyl phenol, dinonyl phenol condensed with 12 moles of EO per mole of phenol, dinonyl phenol condensed with 15 moles of EO per mole of phenol and di-isoctylphenol condensed with 15 moles of EO per mole of phenol. Commercially available nonionic surfactants of this type include Igepal CO-630 (nonyl phenol ethoxylate) marketed by GAF Corporation.

Also among the satisfactory nonionic surfactants are the water-soluble condensation products of a $C_8$–$C_{20}$ alkanol with a heteric mixture of ethylene oxide and propylene oxide wherein the weight ratio of ethylene oxide to propylene oxide is from 2.5:1 to 4:1, preferably 2.8:1 to 3.3:1, with the total of the ethylene oxide and propylene oxide (including the terminal ethanol or propanol group) being from 60 to 85%, preferably 70 to 80%, by weight. Such surfactants are commercially available from BASF-Wyandotte and a particularly preferred detergent is a $C_{10}$ to $C_{16}$ alkanol condensate with ethylene oxide and propylene oxide, the weight ratio of ethylene oxide to propylene oxide being 3:1 and the total alkoxy content being 75% by weight.

Other suitable water-soluble nonionic surfactants which are less preferred are marketed under the trade name "Pluronics." The compounds are formed by condensing ethylene oxide with a hydrophobic base formed by the condensation of propylene oxide with propylene glycol. The molecular weight of the hydrophobic portion of tho molecule is of the order of 950 to 4000 and preferably 200 to 2,500. The addition of polyoxyethylene radicals to the hydrophobic portion tends to increase the solubility of the molecule as a whole so as to make the surfactant water-soluble. The molecular weight of the block polymers varies from 1,000 to 15,000 and the polyethylene oxide content may comprise 20% to 80% by weight. Preferably, these surfactants will be in liquid form and satisfactory surfactants are available as grades L62 and L64.

The anionic surfactant, which is an essential ingredient of present liquid detergent composition, constitutes 1% to 10%, preferably 2% to 9%, most preferably 3% to 8%, by weight thereof and provides good foaming properties. However, preferably reduced amounts are utilized in order to enhance the mildness of the skin property desired in the inventive compositions.

The anionic surfactants which may be used in the nonionic based liquid detergent of this invention are water soluble such as triethanolamine, sodium, potassium, ammonium and ethanolammonium salts of: $C_8$–$C_{18}$ alkyl sulfates such as lauryl sulfate, myristyl sulfate and the like; linear $C_8$–$C_{16}$ alkyl benzene sulfonates; $C_{10}$–$C_{20}$ paraffin sulfonates; alpha olefin sulfonates containing about 10 to 24 carbon atoms; $C_8$–$C_{18}$ alkyl sulfoacetates; $C_8$–$C_{18}$ alkyl sulfosuccinate esters; $C_8$–$C_{18}$ acyl isethionates; and $C_8$–$C_{18}$ acyl taurates. Preferred anionic surfactants are the water soluble salts of: $C_{12}$–$C_{16}$ alkyl sulfates, $C_{10}$–$C_{15}$ alkylbenzene sulfonates, $C_{13}$–$C_{17}$ paraffin sulfonates and alpha $C_{12}$–$C_{18}$ olefin sulfonates. Especially preferred anionic surfactants are ammonium lauryl sulfate and sodium lauryl sulfate.

The water-soluble zwitterionic surfactant, which is also an essential ingredient of present liquid detergent composition, constitutes 0.5% to 10%, preferably 2% to 9%, most preferably 2% to 8%, by weight and provides good foaming properties and mildness to the present nonionic based liquid detergent. The zwitterionic surfactant is a water soluble betaine having the general formula:

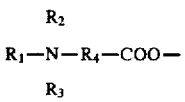

wherein $R_1$ is an alkyl group having 10 to 20 carbon atoms, preferably 12 to 16 carbon atoms, or the amido radical:

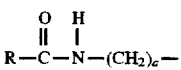

wherein R is an alkyl group having 9 to 19 carbon atoms and a is the integer 1 to 4; $R_2$ and $R_3$ are each alkyl groups having 1 to 3 carbons and preferably 1 carbon; $R_4$ is an alkylene or hydroxyalkylene group having from 1 to 4 carbon atoms and, optionally, one hydroxyl group. Typical alkyldimethyl betaines include decyl dimethyl betaine or 2-(N-decyl-N,N-dimethyl-ammonia) acetate, coco dimethyl betaine or 2-(N-coco N,N-dimethylammonio) acetate, myristyl dimethyl betaine, palmityl dimethyl betaine, lauryl diemethyl betaine, cetyl dimethyl betaine, stearyl dimethyl betaine, etc. The amidobetaines similarly include cocoamidoethylbetaine, cocoamidopropyl betaine and the like. A preferred betaine is coco ($C_8$–$C_{18}$) amidopropyl dimethyl betaine.

The instant compositions contain about 1.5% to about 15.0%, more preferably 2.0% to 12.0% by weight of EUPERLAN PK771™ sold by Henkel. EUPERLAN PK771™ which is a pearlescing agent and is a mixture of a stearate type compound such as ethylene glycol monostearate, glycerol stearate, ethylene glycol distearate, an ethoxylated alkyl ether sulfate surfactant and a mixture of a $(CH_2)_xEO_y$ surfactant, wherein x is 10 to 14 and y is 8 to 12 and a $C_{12-14}$ fatty acid monoalkanol amide, wherein the weight ratio of the $(CH_2)_xEO_y$ surfactant to the $C_{12-14}$ fatty acid monoalkanol amide is about 3:1 to about 1:3, wherein x is about 8 to about 12 and y is about 10 to about 14. The ethylene glycol distearate is present in the detergent composition at a concentration of about 0.5% to about 3%, more preferably about 0.75% to about 2.5% by weight. The mixture of the $(CH_2)_xEO_y$ surfactant and the $C_{12-14}$ fatty acid monoalkanol amide is present in the detergent composition at a concentration of about 0.5% to about 3.0%, more preferably 0.75% to about 2.5% by weight wherein the weight ratio of the $(CH_2)_xEO_y$ surfactant to the $C_{12-14}$ fatty acid monoalkanol amide is about 3:1 to 1:3. The $(CH_2)_xEO_y$ surfactant is different from the water soluble nonionic surfactant used in the instant detergents compositions. The ethoxylated alkyl ether sulfate surfactant is present in the detergent composition at a concentration of about 0.5% to about 3.0%, more preferably 0.75% to about 2.5% by weight.

The metal or ammonium salt of the ethoxylated alkyl ether sulfate which forms a portion of EUPERLAN PK771™ is depicted by the formula:

$$R-(OCHCH_2)_nOSO_3M$$

wherein n is about 1 to about 10, more preferably 1 to 3 and R is an alkyl group having about 8 to about 18 carbon atoms, more preferably 12 to 15 and natural cuts, for example, $C_{12-14}$; $C_{12-15}$ and M is a metal or ammonium cation most preferably sodium or Ammonium. The most preferred embodiment is R is $C_{12-14}$ and X=1 to 3. The ethoxylated alkyl ether sulfate surfactant is present in the composition at a concentration of about 0.5 to 3 wt. %, more preferably about 0.75 to 2.5 wt. %.

The ethoxylated alkyl ether sulfate may be made by sulfating the condensation product of ethylene oxide and $C_{8-10}$ alkanol, and neutralizing the resultant product. The ethoxylated alkyl ether sulfates differ from one another in the number of carbon atoms in the alcohols and in the number of moles of ethylene oxide reacted with one mole of such alcohol. Preferred ethoxylated alkyl ether sulfates contain 12 to 15 carbon atoms in the alcohols and in the alkyl groups thereof, e.g., sodium myristyl (3EO sulfate).

Ethoxylated $C_{8-18}$ alkylphenyl ether sulfates containing from 2 to 6 moles of ethylene oxide in the molecule also are suitable for use in the invention compositions. These surfactants can be prepared by reacting an alkyl phenol with 2 to 6 moles of ethylene oxide and sulfating and neutralizing the resulting ethoxylated alkylphenol.

All of the aforesaid ingredients in this light duty liquid detergent are water soluble or water dispersible and remain so during storage.

This particular combination of a mixture of $C_{12}EO_{10}$ surfactant, $C_{12-14}$ fatty acid monoalkanol amide, ethylene glycol distearate, ethoxylated alkyl ether sulfate surfactant, anionic sulfate surfactant, and betaine surfactant, provides a detergent system having a pearlescence appearance and the system coacts with the nonionic surfactant to produce a liquid detergent composition with desirable foaming, foam stability, detersive properties and mildness to human skin.

Surprisingly, the resultant homogeneous liquid detergent exhibits the same or better foam performance, both as to initial foam volume and stability of foam in the presence of soils, and cleaning efficacy as an anionic based light duty liquid detergent (LDLD) as shown in the following Examples.

The nonionic surfactant, the anionic sulfate surfactant, the betaine surfactant and the EUPERLAN PK771™ are solubilized in the water. To the composition can also be added water soluble hydrotropic salts include sodium, potassium, ammonium and mono-, di- and triethanolammonium salts of xylene sulfonate, benzene sulfonate or cumene sulfonate. While the aqueous medium is primarily water, preferably said solubilizing agents are included in order to control the viscosity of the liquid composition and to control low temperature cloud clear properties. The proportion of solubilizer generally will be from 1% to 15%, preferably 2% to 12%, most preferably 2% to 8%, by weight of the detergent composition with the proportion of ethanol, when present, being 5% of weight or less in order to provide a composition having a flash point above 46° C. Preferably the solubilizing ingredient will be a mixture of ethanol and either sodium xylene sulfonate or sodium cumene sulfonate or a mixture of said sulfonates or ethanol and urea. Inorganic salts such as sodium sulfate, magnesium sulfate, sodium chloride and sodium citrate can be added at concentrations of 0.5 to 4.0 wt. % to modify the cloud point of the nonionic surfactant. Various other ingredients such as urea at a concentration of 0.5 to 4.0 wt. % or urea at the same concentration in combination with ethanol at a concentration of 0.5 to 4.0 wt. % can be used as solubilizing agents. Other ingredients which have been added to the compositions at concentrations of 0.1 to 4.0 wt. % are perfumes, sodium bisulfite, ETDA, isoethanoeic acid and proteins such as lexine protein. The foregoing solubilizing ingredients also facilitate the manufacture of the inventive compositions because they tend to inhibit gel formation.

In addition to the previously mentioned essential and optional constituents of the light duty liquid detergent, one may also employ normal and conventional adjuvants, provided they do not adversely affect the properties of the detergent. Thus, there may be used various coloring agents and perfumes; ultraviolet light absorbers such as the Uvinuls, which are products of GAF Corporation; sequestering agents such as ethylene diamine tetraacetates; magnesium sulfate heptahydrate; pH modifiers; etc. The proportion of such adjuvant materials, in total will normally not exceed 15% by weight of the deterrent composition, and the percentages of most of such individual components will be a maximum of 5% by weight and preferably less than 2% by weight. Sodium formate or formalin can be included in the formula as a perservative at a concentration of 0.1 to 4.0 wt. %. Sodium bisulfite can be used as a color stabilizer at a concentration of 0.01 to 0.2 wt. %.

The present nonionic based light duty liquid detergents such as dishwashing liquids are readily made by simple mixing methods from readily available components which, on storage, do not adversely affect the entire composition. However, it is preferred that the nonionic surfactant be mixed with the solubilizing ingredients, e.g., ethanol prior to the addition of the water to prevent possible gelation. The nonionic based surfactant system is prepared by sequentially adding with agitation the anionic sulfate surfactant, the betaine surfactant and EUPERLAN PK771™ to the aqueous solution of the nonionic surfactant which has been previously mixed with a solubilizing agent such as ethanol and/or sodium xylene sulfonate to assist in solubilizing said surfactants, and then adding with agitation the formula amount of water to form an aqueous solution of the nonionic based surfactant system. The use of mild heating (up to 100° C.) assists in the solubilization of the surfactants. The viscosities are adjustable by changing the total percentage of active ingredients. In all such cases the product made will be pourable from a relatively narrow mouth bottle (1.5 cm. diameter) or opening, and the viscosity of the detergent formulation will not be so low as to be like water. The viscosity of the detergent desirably will be at least 100 centipoises (cps) at room temperature, but may be up to 1,000 centipoises as measured with a Brookfield Viscometer using a number 3 spindle rotating at 12 rpm. The viscosity of the detergent composition may approximate those of commercially acceptable detergent compositions now on the market. The viscosity of the detergent composition and the detergent composition itself remain stable on storage for lengthy periods of time, without color changes or settling out of any insoluble materials. The pH of this formation is substantially neutral to skin, e.g., 4.5 to 8 and preferably 5.0 to 7.0. The pH of the composition can be adjusted by the addition of $Na_2O$ (caustic soda) to the composition.

These products have unexpectedly desirably properties. For example, the foam quality and detersive property is equal to or better than standard light duty liquid detergents while using a nonionic surfactant as the primary surfactant and minimal amounts of anionic surfactant, thereby achieving a mild, non-irritating liquid detergent composition.

The following examples are merely illustrative of the invention and are not to be construed as limiting thereof.

DESCRIPTION OF THE PREFERRED EMBODIMENTS

EXAMPLE 1

The following formulas were prepared at room temperature by simple liquid mixing procedures as previously described

1. GREASY SOIL

Soil composition: ⅓ olive oil, ⅓ butter, ⅓ soft beef tallow
5 grams of soil is put on each plate/Detergent concentration: 0.5 grams of soil/liter of water; used 5 liters of water at 50° C. to start.

2. MIXED SOIL

Soil composition (for 1 KG): 112.5 grams of olive oil; 112.5 grams of lard; 225 grams of wheat flour; 50 grams of skimmed powdered milk; and 50 grams of tap water.

7.5 grams of soil is put on each plate/Detergent concentration: 0.5 grams of soil/liter of water; used 5 liters of water at 50° C.

In the Zein test (In vitro mildness test) a Zein (a protein very similar to keratin present in skin and hair) is denatured (solubilized) by irritant products (mainly surfactants). The higher the Zein dissolved by the LDLD solution, the higher the predicted irritation potential. Originally the solubilized Zein was determined by the Kjeldahl method (nitrogen assay). The method has been replaced by a Colorimetric technique, the BCA Protein assay from Pierce (Post Office Box 117, Rockford, Ill. 61105 USA-Ref. 23225).

Literature Ref.: Kaestner and Frosch (1981) Hautirritationen Verschiedener Anionaktiver Tensiden In Duhring Kammer Testam Menschen In Vergleich Zu In Vitro Und Tierenexperimentellen Methoden. Fette-Seifen Und Anstrichmittel, 83, 33.

The Foam Longevity—Miniplate Test aims at assessing the foam stability of a LDLD solution in presence of a fatty soil. The soil is a vegetable shortening: Crisco (from U.S.). This soil is injected in the LDLD solution with a syringe at a flow rate of 0.6 grams/minute. 10 ml of a 5% LDLD solution are added to 400 ml of water (=1.25 gr/l of LDLD). During 1 minute foam is generated with a brush (according to a hypocycloidal pattern). The brush keeps moving to help fat emulsification. Fatty soil is then injected in the solution at a constant flow rate up to disappearance of the foam. Foam generation and disappearance are evaluated by photo electrical cell and recorded automatically.

The miniplate number is determined by the formula

|  | Prot 1 | Prot 2 | Prot 3 | Prot 4 | Prot 5 | Prot 6 | Commercial Product Pril Balsam |
|---|---|---|---|---|---|---|---|
| Dobanol 1-9 | 14 | 9 | 18.5 |  |  |  |  |
| Dobanol 91-8 |  | 5 |  | 10.5 |  |  |  |
| Ammonium lauryl sulfate | 6 | 6 | 4.7 |  |  |  |  |
| Sodium lauryl sulfate |  |  |  | 7.9 |  |  |  |
| Lauryl dimethyl betaine | 5 | 5 | 4.8 | 6.6 |  |  |  |
| LMMEA |  |  | 1.9 |  |  |  |  |
| Paraffin sulfonate |  |  | 1.1 |  | 24 | 20 |  |
| Sodium lauryl ethoxylated sultate (2E0) |  |  |  |  | 6 | 5 |  |
| EUPERLAN PK771 ™ | 5 | 5 | 5 | 5 | 5 | 5 |  |
| Perfume | 0.2 | 0.2 | 0.2 | 0.2 | 0.15 | 0.15 |  |
| Dye | QS | QS | QS | QS | QS | QS |  |
| Miniplate | 35 | 35 | 40 | 37 | 42 | 33 | 18 |
| Handwash (grease) | 14 | NA | 17 | 12 | 21 | 17 | 14 |
| Handwash (mixed soil) | 14 | NA | 18 | 14 | 12 | 10 | 14 |
| Zein index (in vitro) mildness | 375 | NA | 400 | 250 | 100 | 120 | 200 |

In the hand dishwashing method the soiled plates are washed thoroughly with a terry cloth (back and front of the plates) in a dishpan. Initial foam is generated only by gravity: the water is dropped in the dishpan where the product was previously weighed, number of plates washed to reach foam end point is recorded. Two types of soils are used: greasy soil and mixed food soil.

$$MP=(GC \times GF \times AET)/0.12$$

wherein GC=grease coefficient; GF=grease flow equal to (total injected grease weight)/(T2−T0); AET=time measured from the beginning of grease injection (to) and the end of foam detection (T1); 0.12=correlation coefficient to relate the calculated miniplate number to the number of dishes washed by hand in similar conditions; T2=end of test, grease injection is stopped.

Extrapolation

The actual plate number can be easily extrapolated from miniplate number by assuming that each large plate is soiled with 3 grams of soil (fat).

(number of miniplates)×(weight of product)×0.08

What is claimed is:

1. A high foaming, nonionic surfactant based, light duty, liquid detergent composition comprising approximately, by weight,
   (a) 10% to 30% of a water-soluble nonionic surfactant;
   (b) 1% to 10% of an alkyl sulfate surfactant;
   (c) 0.5% to 10% of an alkyl betaine surfactant;
   (d) 0.5% to 3% of an ethylene glycol distearate;
   (e) 0.2% to 3% of a mixture of a $(CH_2)_xEO_y$ surfactant and a $C_{12-14}$ fatty acid monoalkanol amide, wherein the $(CH_2)_xEO_y$ surfactant is different from the water soluble nonionic surfactant and the weight ratio of $(CH_2)_xEO_y$ surfactant to said $C_{12-14}$ fatty acid monoalkanol amide is about 3:1 to about 1:3 and x is 10 to 14 and y is 8 to 12;
   (f) 0.5% to 3.0% of an ethoxylated alkyl ether sulfate surfactant; and
   (g) the balance being water wherein the composition exhibits a pearlescence appearance and excluded from the compositions are cetearyl alcohol, tricetyl methyl ammonium chloride, a silicone conditioning agent such as polydimethyl siloxane, polyalkyl siloxane, polyaryl siloxane, polyalkylaryl siloxane, polyether siloxane copolymer, peroxy oxidizing agents such as hydrogen peroxide and sodium percarbonate, sodium perborate and perbenzoic acid, and selenium sulfide.

2. A liquid detergent composition according to claim 1 which includes, in addition, 1% to 15% by weight of a solubilizing agent which is a water soluble salts of $C_1$–$C_3$ substituted benzene sulfonate hydrotropes and mixtures thereof.

3. A liquid detergent composition according to claim 1 wherein said water-soluble nonionic surfactant is a condensate of a primary $C_8$–$C_{18}$ alkanol with 5–30 moles of ethylene oxide.

4. A liquid detergent composition according to claim 3 wherein said anionic surfactant is a $C_8$–$C_{18}$ alkyl sulfates.

5. A liquid detergent composition according to claim 1 wherein said water-soluble nonionic surfactant is present in an amount of 16% to 22% by weight, said anionic sulfate surfactant is present in an amount of 2% to 9% by weight and said betaine surfactant sulfate is present in an amount of 2% to 9% by weight.

6. A liquid detergent composition according to claim 5 wherein said anionic detergent is a $C_{12}$–$C_{16}$ alkyl sulfate.

7. A liquid detergent composition according to claim 1 further including a perservative.

8. A liquid detergent composition according to claim 1 further including a color stabilizer.

9. A liquid detergent composition according to claim 4, wherein said betaine surfactant is lauryl dimethyl betaine.

* * * * *